(12) United States Patent
Yaegashi

(10) Patent No.: US 8,226,542 B2
(45) Date of Patent: Jul. 24, 2012

(54) CARDIAC ASSIST SYSTEM WITH CELL TRANSPLANTATION ASPECTS

(75) Inventor: Mitsutoshi Yaegashi, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 875 days.

(21) Appl. No.: 12/237,823

(22) Filed: Sep. 25, 2008

(65) Prior Publication Data

US 2009/0088596 A1   Apr. 2, 2009

(30) Foreign Application Priority Data

Sep. 27, 2007 (JP) ................................ 2007-252604

(51) Int. Cl.
*A61N 1/362* (2006.01)

(52) U.S. Cl. ........................................................ 600/16

(58) Field of Classification Search .......... 607/3; 600/9, 600/12, 16
See application file for complete search history.

(56) References Cited

U.S. PATENT DOCUMENTS

| | | | | |
|---|---|---|---|---|
| 4,621,617 A * | 11/1986 | Sharma | ............................ | 600/16 |
| 4,829,984 A * | 5/1989 | Gordon | ............................ | 600/12 |
| 5,112,202 A | 5/1992 | Oshima et al. | | |
| 5,810,708 A * | 9/1998 | Woodard et al. | ................. | 600/16 |
| 6,099,460 A * | 8/2000 | Denker | ............................ | 600/17 |
| 6,123,724 A * | 9/2000 | Denker | ......................... | 623/3.11 |
| 6,309,341 B1 * | 10/2001 | Denker | ............................ | 600/16 |
| 6,371,905 B1 * | 4/2002 | March | .............................. | 600/9 |
| 2002/0156339 A1 * | 10/2002 | Kim | .................................. | 600/12 |
| 2005/0119518 A1 * | 6/2005 | Sen et al. | ........................... | 600/9 |
| 2008/0006281 A1 * | 1/2008 | Sih et al. | ........................ | 128/899 |
| 2009/0012498 A1 * | 1/2009 | Sawa et al. | ..................... | 604/522 |

* cited by examiner

*Primary Examiner* — Eric D Bertram
*Assistant Examiner* — Roland Dinga
(74) *Attorney, Agent, or Firm* — Buchanan Ingersoll & Rooney PC

(57) ABSTRACT

A ventricular assist system includes a controller supplying a DC voltage or an AC voltage, and electromagnets adapted to be adhered to an infarct portion of a heart at the time of embedding a pump. After embedding the system, cells enclosed in capsules are released into the surroundings of the infarct portion by use of a catheter. The capsules are magnetic so that they can be concentrated onto the infarct portion by magnetic fields of the electromagnets, and are broken in the vicinity of the infarct portion, whereby cells effective for regeneration of cardiac muscles can be conveyed to the infarct portion in a noninvasive manner after the embedding of the ventricular assist system.

16 Claims, 9 Drawing Sheets

F I G. 3
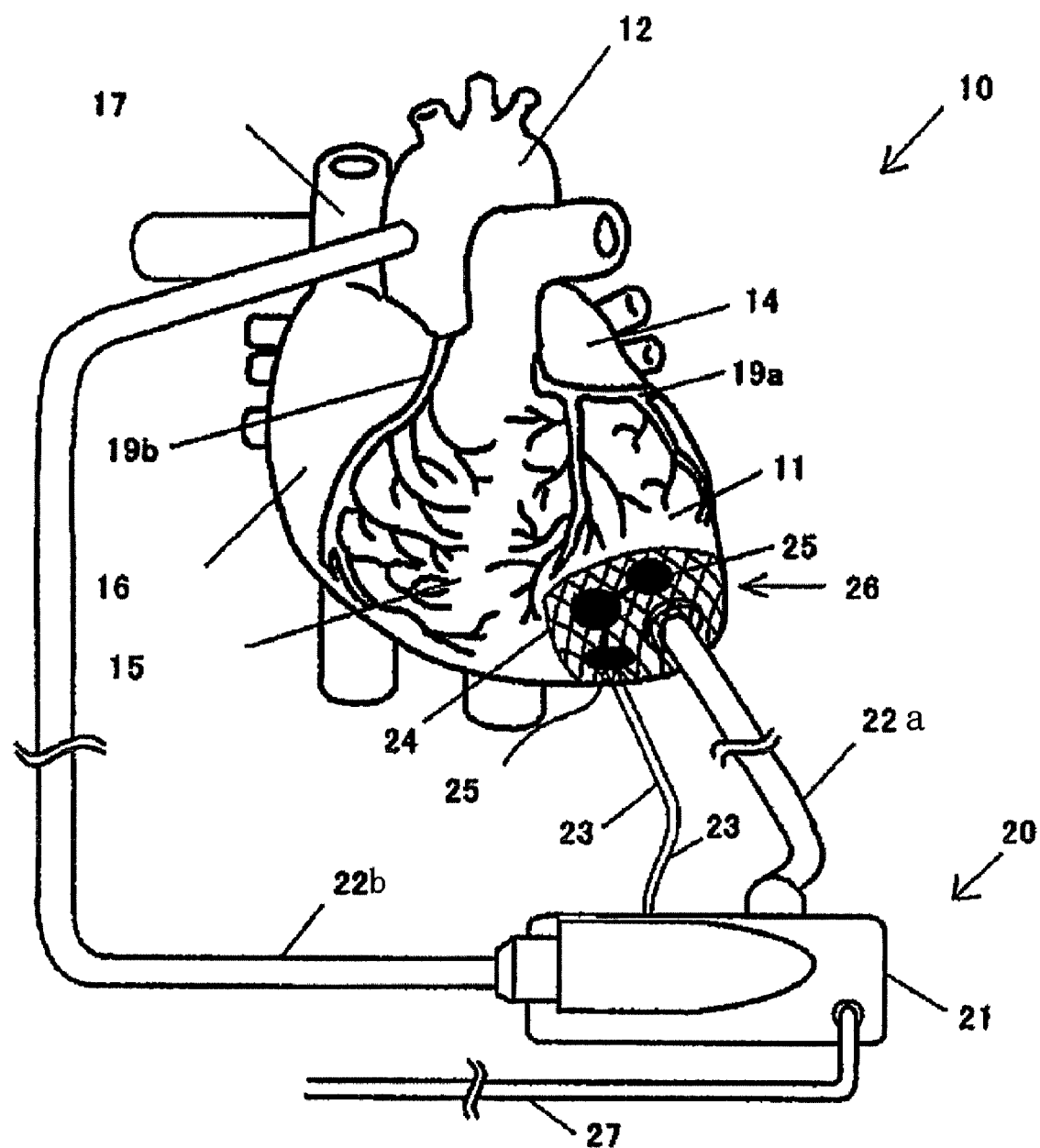

F I G. 5
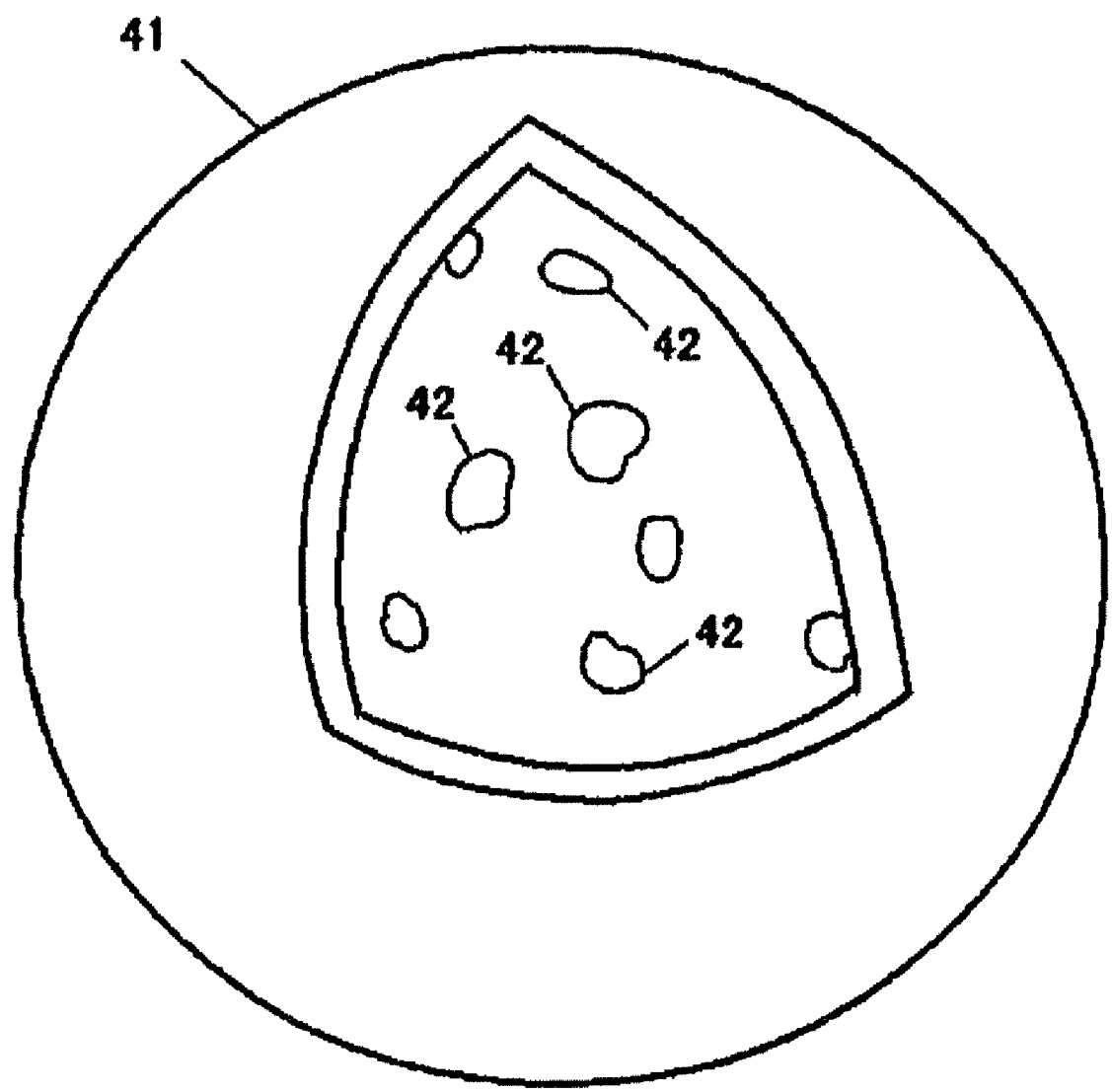

F I G. 8
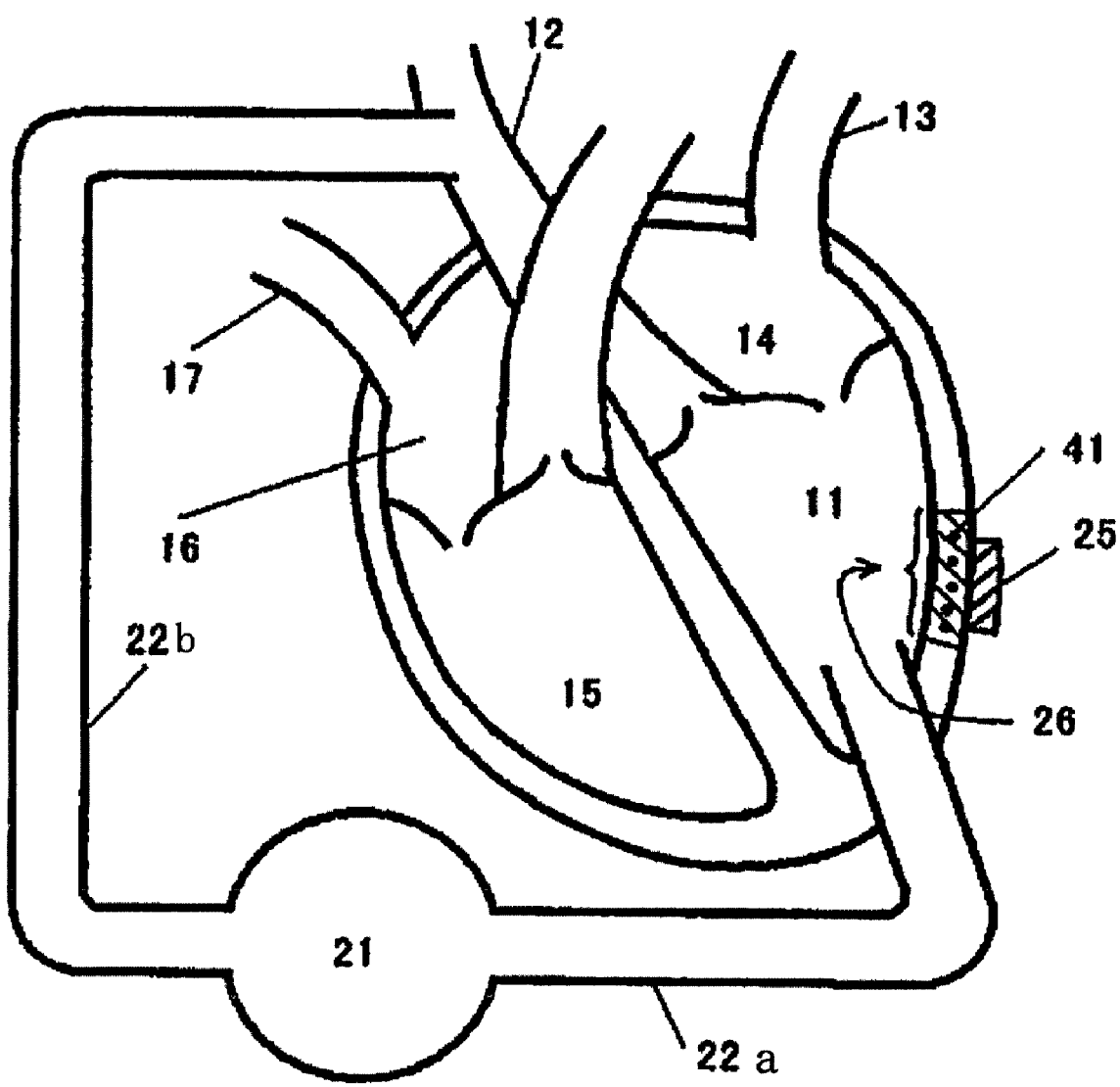

CARDIAC ASSIST SYSTEM WITH CELL TRANSPLANTATION ASPECTS

TECHNOLOGICAL FIELD

The present invention generally pertains to a cardiac assist system. More specifically, the invention relates to a cardiac assist system which includes an intracorporeally embedded type pump, as a ventricular assist system, and by which cardiac muscles can be regenerated noninvasively.

BACKGROUND DISCUSSION

Cardiac muscle cells are incapable of growth and differentiation by themselves. Therefore, when the cardiac muscle cells are damaged, they cannot be regenerated and, hence, dysfunction (heart failure) may be induced. To cure this diseased state, replacement type therapies such as heart transplantation, use of an artificial (mechanical) heart, etc. have been employed. However, heart transplantation is problematic due to an insufficient number of donors. The use of an artificial heart suffers from the disadvantage that quality of life is lowered.

Three techniques composed of cell transplantation, alleviation of ventricular load by use of a ventricular assist system, and hemocathasis by plasmapheresis are considered effective for achieving regeneration of cardiac muscles. Here, hemocathasis by plasmapheresis is a technique for cleaning the blood serving as a culture medium and for permitting the cells to function more easily; therefore, the former two techniques alone may be sufficient to obtain the desired effect. Where this therapy is performed, the ventricular assist system is removed when it is confirmed that the cardiac muscles have sufficiently been regenerated and the functions of the patient's own heart have restored.

As for the cell transplantation, among the above-mentioned techniques, there are a number of methods. An example of one method involves sampling bone marrow from the hipbone, separating the marrow cells, and injecting the marrow cells through a catheter into a coronary bypass formed at the time of a surgical operation of embedding the ventricular assist system. In another example, thoracotomy is again performed after the ventricular assist system embedding operation, and myoblast and marrow cells are supplied by injection into a multiplicity of portions (for example, 60 portions) of the wall of the heart.

The first method mentioned by way of example has merit in that it is less invasive due to the absence of thoracotomy. However, it is difficult to concentrate the cells into the region of myocardial infarction. On the other hand, in the latter method mentioned above, injection of the cells is performed by way of thoracotomy, so that the growth factor secreted after injection into comparatively remote portions of the wall of the heart infiltrates into the infarct portion, which is effective. Even in the latter method, however, the cells are not sufficiently concentrated into the infarction portion. Besides, the latter method has the disadvantage of being heavily invasive, since it requires thoracotomy.

If the injection of the cells can be carried out at the time of embedding the ventricular assist system, the cells can be injected directly into the infarct portion. However, injecting the cells simultaneously while embedding the ventricular assist system is difficult to achieve, since the culture of cells takes a few weeks, and, in practice, the ventricular assist system must often be embedded with unexpected timing.

Chisato Nojiri, Journal of Japan Surgical Society, Vol. 103, No. 9, pp. 607-610, 2002 contains a description of a ventricular assist system which includes a magnetic levitation type pump.

SUMMARY

According to one aspect, a cardiac assist system for assisting activity of a heart includes a cardiac activity assisting unit configured to be connected to the heart and operative to assist the activity of the heart, an electromagnet configured to be fixed to a surface of the heart, and a controller electrically connected to the cardiac activity assisting unit and the electromagnet, and operative to control the cardiac activity assisting unit and the electromagnet.

In accordance with another aspect, a cardiac assist system for assisting activity of a heart in a living body comprises a pump configured to be implanted in the living body and fluidly connected to the heart, a plurality of electromagnets mounted on a carrier that is fixable to a surface of the heart, a hollow magnetic capsule configured to contain cells effective for regeneration of cardiac muscles, and a controller electrically connected to the pump and the electromagnets to operate the pump and supply voltage to the electromagnets to produce a magnetic field by which the magnetic capsule is attracted towards the electromagnets.

Another aspect involves a method of assisting heart activity comprising fluidly connecting a cardiac activity assisting unit to a heart in a living body, fixing at least one electromagnet to the heart in the living body, operating the cardiac activity assisting unit, introducing a contents-containing magnetic capsule into the body, producing a magnetic field through use of the electromagnet to move the magnetic capsule towards the electromagnet, and breaking open the magnetic capsule to release the contents.

The ventricular assist system and method disclosed here allows cells necessary for regeneration of cardiac muscles to be positioned at an infarct portion in a sufficient density and without need for thoracotomy. In addition, the ventricular assist system can be removed after regeneration of the cardiac muscles.

BRIEF DESCRIPTION OF THE DRAWINGS

FIG. 3 is a general illustration of the condition where electromagnets are disposed together with the ventricular assist system according to one embodiment disclosed here.

FIG. 5 is a partly cross-sectional view of a capsule in which cells are enclosed in one embodiment disclosed here.

FIG. 8 is a schematic illustration in which the catheter has reached the coronary artery and capsules are released according to according to an embodiment disclosed here.

DETAILED DESCRIPTION

As disclosed here, electromagnets are attached to an infarct portion, together with a cardiac activity assisting unit. In this way, cells effective for regeneration of cardiac muscles can be concentrated into a desired region, by use of magnetic capsules. In addition, when a drug is enclosed in the capsules, an effective medication can be achieved.

The description below describes one embodiment of a cardiac assist system (hereinafter referred to as "the present embodiment"), along with a description of a capsule guiding method and effects of the system on therapy.

Ventricular Assist System

Figure 1:
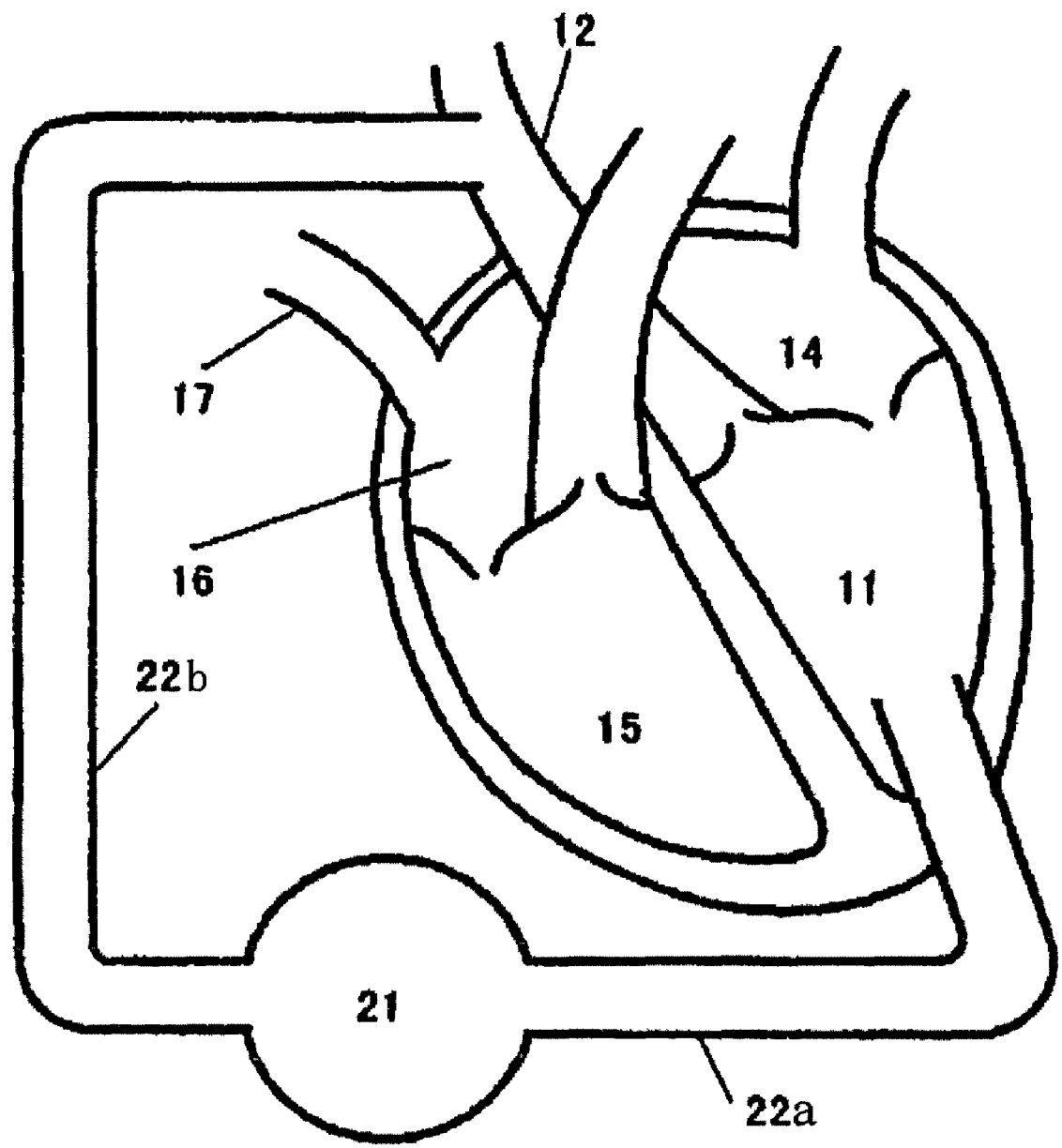
FIG. 1 is a schematic illustration of a left ventricular assist system according to one embodiment disclosed here.

First, a cardiac assist system according to the present embodiment will be described referring to FIGS. 1 to 3. In the present embodiment, the cardiac assist system is in the form of a ventricular assist system. FIG. 1 schematically illustrates a left ventricular assist system.

Briefly describing the flow of blood, blood having undergone gas exchange in the lung and containing oxygen flows from the pulmonary veins into the left atrium 14. Next, the blood flows from the left atrium 14 into the left ventricle 11, and is forced out therefrom into the aorta 12. Thereafter, the blood is circulated throughout the patient's body, before flowing through the vena cava 17 into the right atrium 16. Then, the blood flows from the right atrium 16 into the right ventricle 15, and is forced out therefrom into the pulmonary artery.

The heart is a pump that feeds the blood to the whole body. When this function is lowered due to myocardiac infarction or the like, blood circulation is worsened of adversely affected. Therefore, when the function of the heart is lowered due to myocardiac infarction or the like, a pump 21 is disposed between the left ventricle 11 and the aorta 12 so as to assist the heart. With this arrangement in which the pump is fluidly connected to the heart, it is possible to assist the function or operation of the heart, specifically the function of the left ventricle 11 to feed the blood to the whole body.

Figure 2:
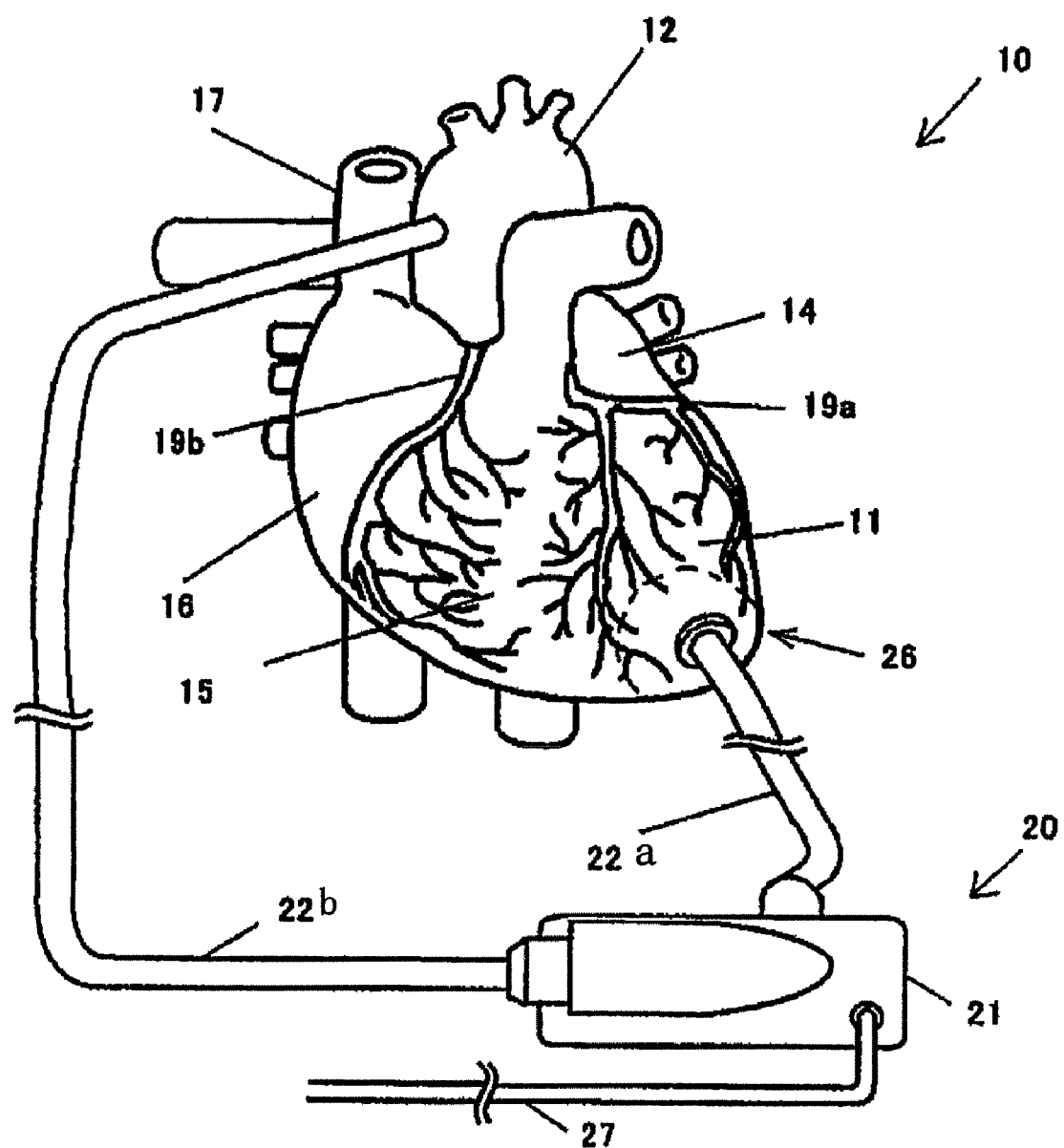
FIG. 2 is a general illustration of the ventricular assist system attached to a heart having an infarct portion.

FIG. 2 generally illustrates a condition where the ventricular assist system is attached to a heart 10 which has an infarct portion 26. This illustrated embodiment presumes that the infarct portion 26 lies in the left ventricle 11. When such an infarct portion 26 is present, the force with which the heart 10 pumps out the blood is weakened or reduced. In such a situation, therefore, the pump 21 (cardiac activity assisting unit) for feeding the blood from the left ventricle 11 into the aorta 12 is arranged to assist the cardiac function. This helps ensure that the function of the heart 10 to feed the blood to the whole body can be brought into a normal state.

The ventricular assist system 20 comprises the pump 21 and conduits (connection tubes) 22, i.e., tubes through which blood flows. The conduits 22 are connected to the left ventricle 11 and the aorta 12, respectively. The conduits 22 are installed by providing openings in the cardiac wall of the left ventricle 11 and in the blood vessel wall of the aorta 12. In other words, the conduits 22 are tubes for the blood to flow therethrough, like a blood vessel.

In the present embodiment, electromagnets 25 are disposed at the infarct portion 26 so that capsules 41 (shown in FIG. 5) enclosing the cells effective for regeneration of cardiac muscles are guided to the infarct portion 26 under the action of the magnetic field.

FIG. 3 is a general illustration of the condition where the electromagnets 25 are disposed together with the ventricular assist system 20. As illustrated, the electromagnets 25 are disposed on the infarct portion 26 of the heart. While FIG. 3 illustrates three electromagnets 25, the number of the electromagnets 25 is not particularly limited insofar as the number of electromagnets is sufficient to cover the infarct portion 26 with the electromagnets 25.

One example for installing the electromagnets 25 involves attaching the electromagnets 25 to a carrier 24 which, in this illustrated embodiment, is a sheet, and adhering the integral assembly of the sheet 24 and the electromagnets 25 to the surface of the heart 10. Examples of materials which can be used for the sheet include a nonwoven fabric or the like. In addition, the electromagnets 25 can be fixed also by use of a net. In addition, the electromagnets 25 may be adhered by use of a medical adhesive or the like.

Generally speaking, the electromagnets 25 attract the magnetic capsules 41 by their magnetic forces and break the capsules in situ so that the cells or a drug enclosed in the capsules 41 are released into a desired region. Therefore, the manner of attaching the electromagnets 25 is not limited to that in the present embodiment.

Figure 4:
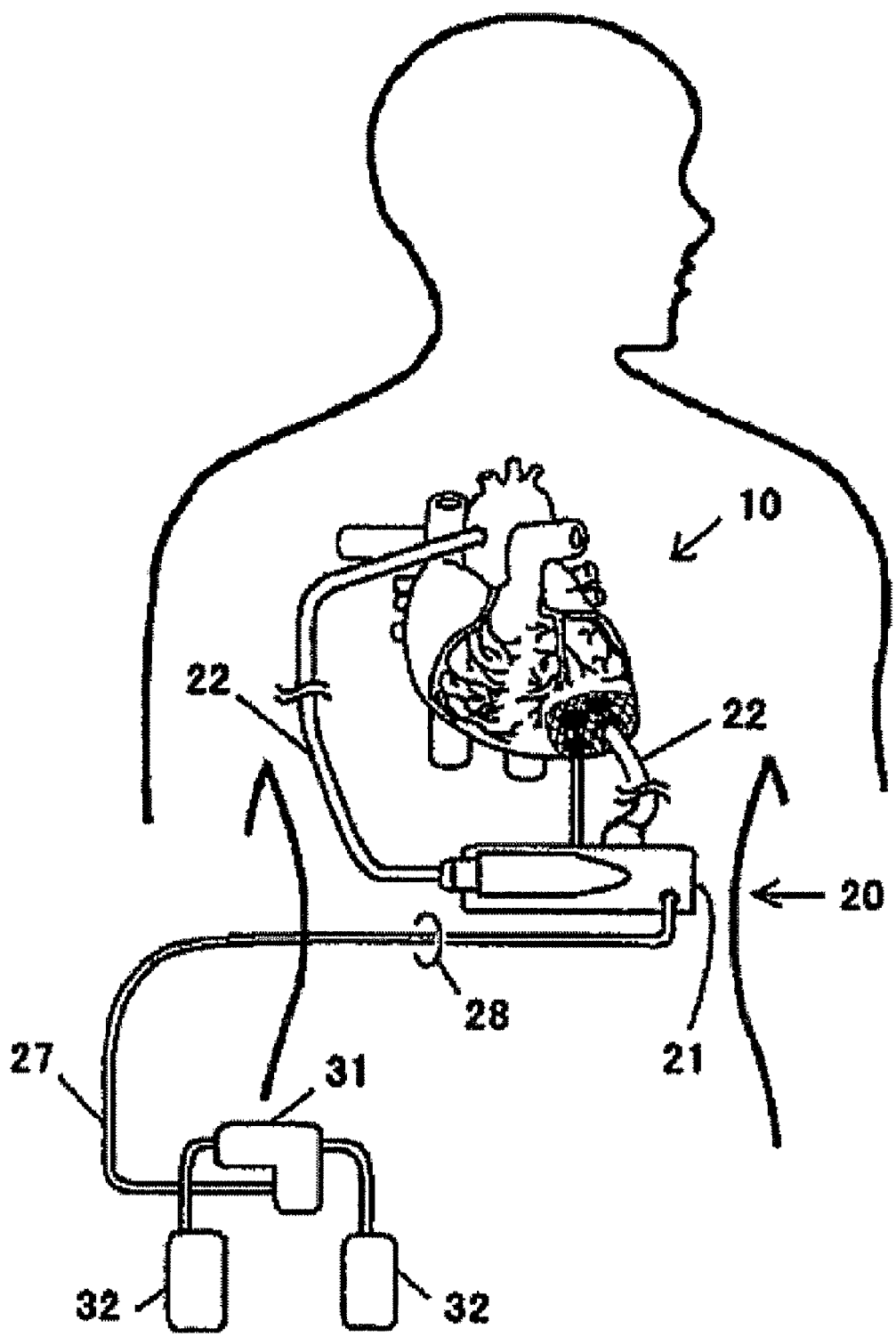
FIG. 4 is a schematic illustration of the ventricular assist system and the electromagnets attached to a human body according to one embodiment.

In addition, as above-mentioned, in the present embodiment, the electromagnets 25 for guiding the capsules are attached to the infarct portion 26 together with the sheet 24, and three electromagnets 25 are connected in series. As for cables 23, two cables (namely, a plus (positive) cable and a minus (negative) cable) provide connection between the series connected electromagnets 25 and the pump 21. A cable 27 providing connection between the pump 21 and a controller 31 extends from the inside of the body to the exterior of the body through a body surface. In other words, as generally illustrated in FIG. 4, an opening 28 through which passes the cable 23 is formed in the body surface. The cables 23 for the capsule-guiding electromagnets 25 lead out to the exterior of the body through the opening 28 and are connected to the controller 31, which is operative to generate a DC current or an AC current.

FIG. 4 is a schematic illustration of the condition where the ventricular assist system 20 is attached to a human body. The pump 21 is connected to the heart 10 through the conduit 22a, which is connected to the inlet (inflow port) of the pump 21, and the conduit 22b which is connected to the outlet (outflow port) of the pump 21. In addition, the pump 21 is connected to the controller 31, preferably a portable type controller, through the cable 27. The portable type controller 31 is connected to a power source 32 for supplying electric power. In the example shown in FIG. 4, two power sources 32 are connected to the controller 31.

Guiding of Capsules

A method for feeding the microcapsules 41 to the infarct portion 26 by use of the ventricular assist system 20 is now described. The microcapsules 41 generally have a spherical shell-like hollow shape, as shown in FIG. 5. The capsules are made of magnetic material. In the inside space (hollow interior) of the spherical shell, for example, cells 42 effective for regeneration of cardiac muscles, such as marrow cells, are enclosed. Examples of materials for the capsules 41 include a material which is innoxious to human body and is magnetic, for example iron oxide. As for the size of the capsules 41, the diameter may be in the range of 100 to 5000 nm. Examples of the cells 42 to be enclosed in the capsules 41 include cells obtained by sampling the bone marrow from the hipbone and separating the marrow cells. The cells are preferably cultured before use.

The capsules 41 with the marrow cells enclosed therein are fed directly to the infarct portion 26 by use of a catheter 43 or the like. The catheter 43 may be any one of the ordinarily used catheters. In the case of myocardiac infarction, the catheter 43 is introduced through an artery in the upper half or lower half of the patient's body, and is passed through the aorta 12 to reach the coronary artery 19. Thereafter, the microcapsules 41 are injected from a syringe 44.

Figure 6:
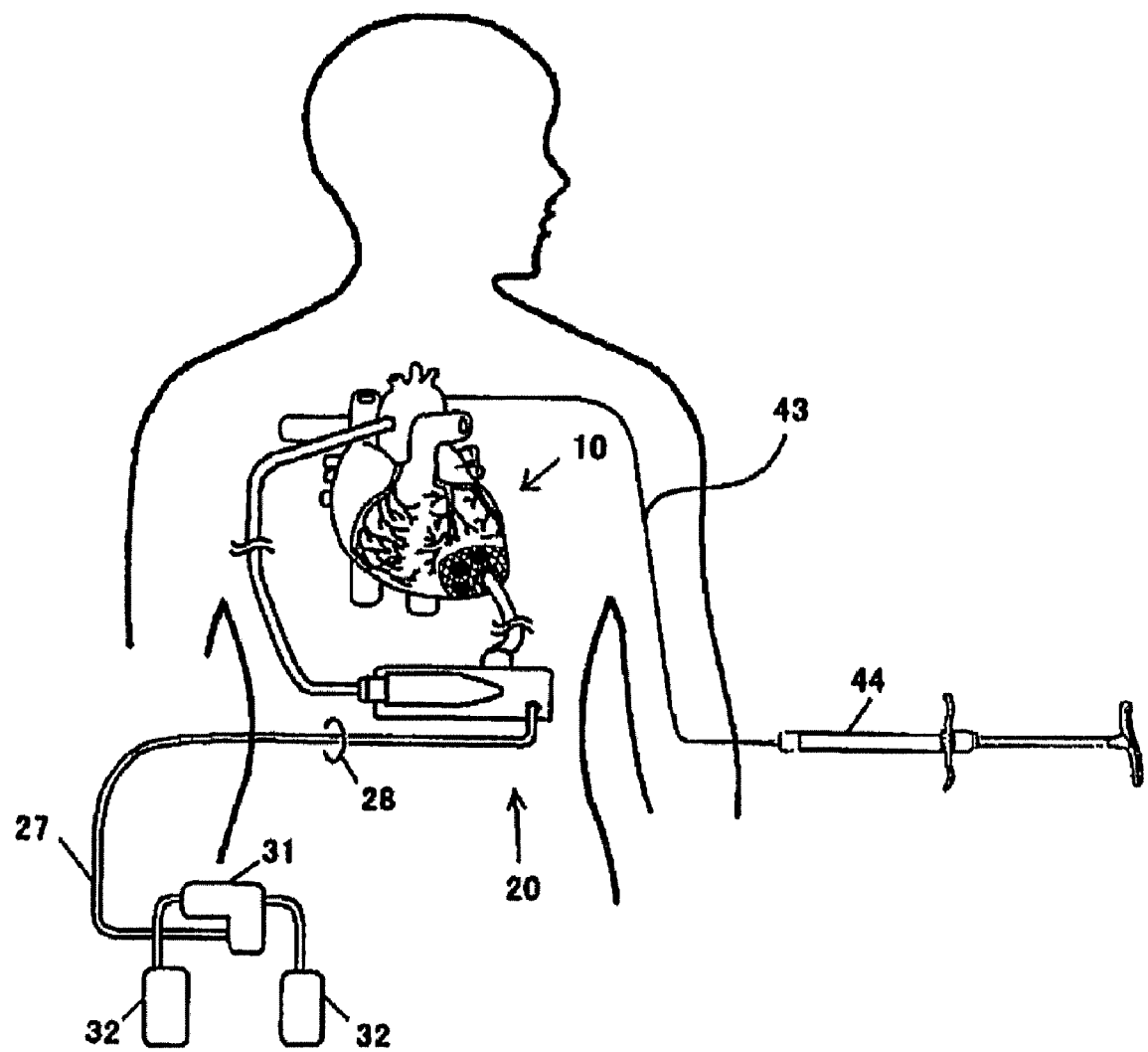
FIG. 6 is a general illustration of a catheter inserted in the arrangement shown in FIG. 4.
Figure 7:
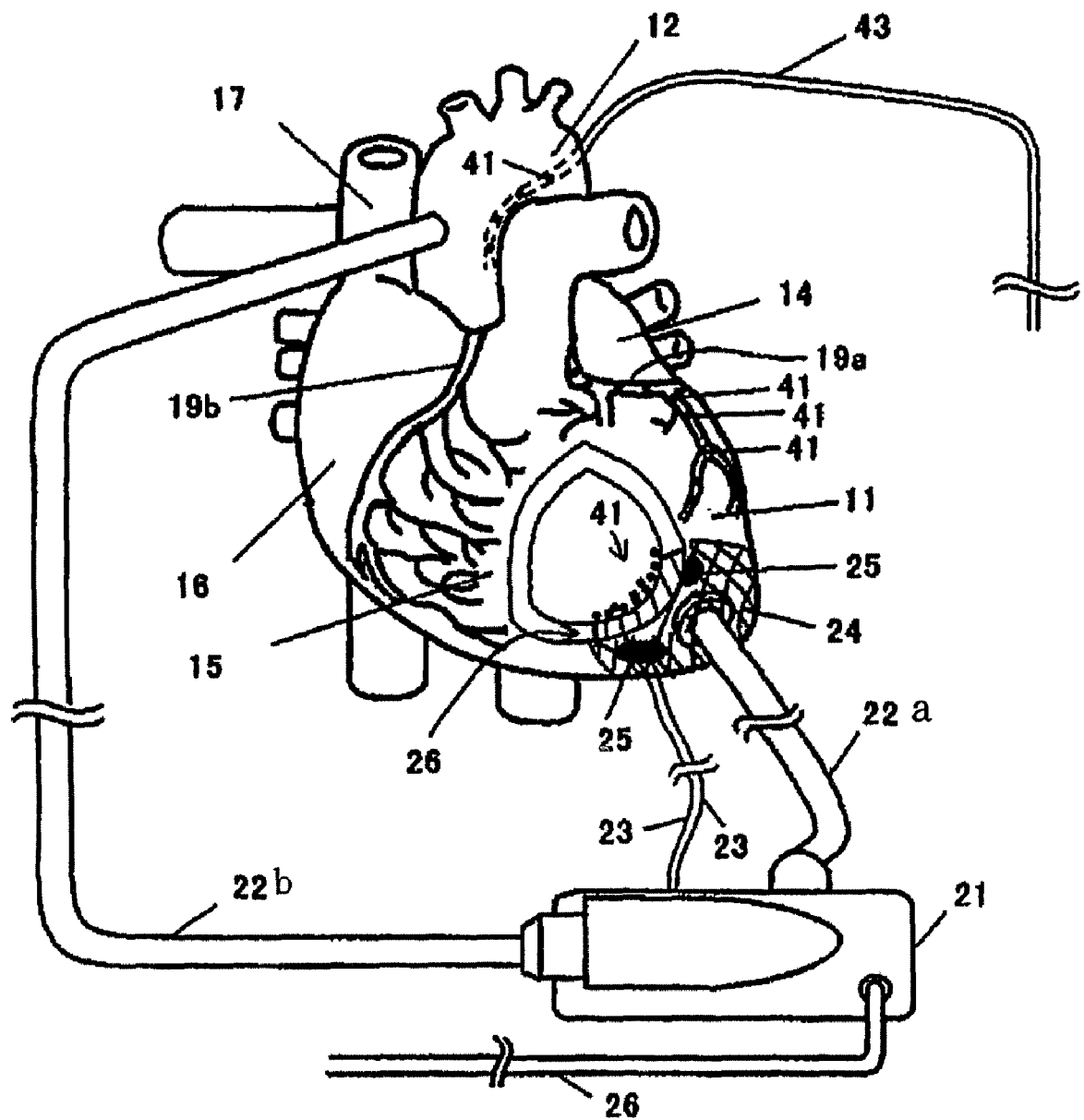
FIG. 7 is a general illustration of when the catheter has reached the coronary artery and capsules are released according to one embodiment disclosed here.
Figure 9:
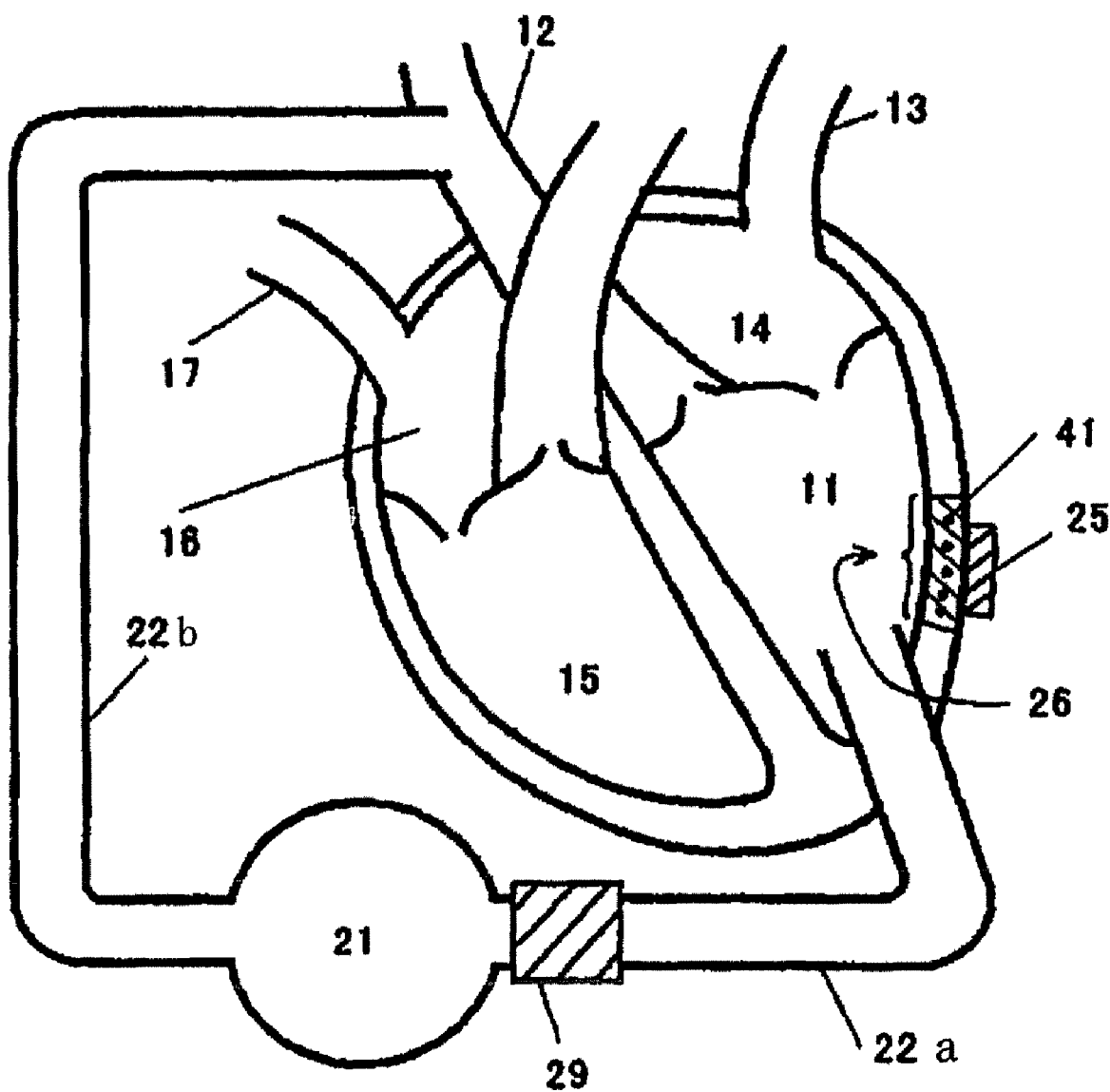
FIG. 9 is a schematic illustration in which a permanent magnet is disposed at an inlet of a pump according to an embodiment disclosed here.

The condition where the catheter is introduced is shown in FIGS. 6, 7 and 8. FIG. 6 is a general illustration of the catheter 43 as it is inserted, and FIG. 7 is a partly cross-sectional illustration of a condition where the catheter 43 has reached the coronary artery 19 (in FIG. 7, the left coronary artery 19*a*) and the capsules 41 are released in the present embodiment. FIG. 8 schematically illustrates a condition where the catheter has reached the coronary artery 19 and the capsules 41 are released. The capsules 41 are fed through the catheter 43 to be released in the coronary artery 19, and, further, passed through branched blood vessels to be released into the vicinity of the infarct portion 26 of the left ventricle 11. In this instance, a DC current is supplied to the electromagnets 25, whereon the capsules 41 are attracted by the magnetic forces of the electromagnets 25 and are concentrated onto the infarct portion 26.

When the capsules 41 are concentrated onto the infarct portion 26, an AC current or a pulsed current is supplied to the electromagnets 25, whereby the capsules 41 are broken. As a result, the cells 42 enclosed in the capsules 41 are released to the outside so that the cells 42 can be efficiently fixed to the infarct portion 26. With the capsules 41 thus broken, the marrow cells 42 previously enclosed in the capsules are released to the periphery of the infarct portion 26. Consequently, regeneration of the cardiac muscles is effected.

At the time of therapy, it is desirable that the opening end of the catheter 43 reaches the periphery of the infarct portion 26. However, in practice, this can be difficult to achieve or realize. Utilizing the system and method disclosed here, however, it is possible to guide the capsules 41 by the magnetic fields of the electromagnets 25 and thereby concentrate or desirably position the capsules 41 onto the infarct portion 26. This helps facilitate non-invasive performance of the appropriate therapy after the ventricular assist system 20 and the electromagnets 25 are embedded. In addition, since such a therapy can be carried out repeatedly, it is possible to regulate the amount of the marrow cells injected, while observing the recovered state of the cardiac muscles.

While the material enclosed in the capsules is described above as being marrow cells in the present embodiment, the material naturally is not limited to marrow cells and may be other effective cells or other drug or the like.

Effects on Therapy

Now, a specific therapeutic method will be described.

(1) At the time of embedding the ventricular assist system 20, the electromagnets 25 for guiding the capsules 41 are adhered to the infarct portion 26.

(2) Cells effective for regeneration of cardiac muscles (for example, marrow cells) are cultured.

(3) The cells 42 thus cultured are enclosed in the capsules 41. The capsules 41 are magnetic and can be moved by a DC magnetic field. As the material of the capsules 41, a polymer containing nano-particles of iron oxide may be used. Iron oxide is innoxious to the living body, and the polymer is desirably selected to be innoxious to the living body. The capsules 41 are 100 to 5000 nm in size.

(4) Using the catheter 43, the capsules 41 are delivered to or released into the vicinity of the infarct portion 26. Thereafter, a DC current is supplied to the electromagnets 25 which have been previously disposed at positions selected to guide the capsules 41. The capsules 41 are thus moved to the infarct portion 26. Furthermore, an AC current or a pulsed current is supplied to the electromagnets 25, to thereby break the capsules 41.

(5) Step (4) above is repeated according to the extent of recovery of the cardiac muscles.

(6) At the time when the function of the heart 10 has been improved to such a level that the ventricular assist system 20 can be stopped, thoracotomy is performed and the ventricular assist system 20 is removed together with the electromagnets 25 set for guiding the capsules 41.

The pump can be operated once it is embedded (i.e., the pump can be operated from step 1). Also, the method or process discussed above can be implemented such that a period of time (e.g., three months) passes between step 1 and step 2 discussed above. While the electromagnets 25 for guiding the capsules 41 are preferably connected in series to reduce the number of wires in the present embodiment, the electromagnets 25 may also be connected in parallel. Parallel connection makes it possible to prevent the reliability from being lowered due to wire breakage or the like.

Known ventricular assist systems include those of the type in which a magnetic force of a magnetic bearing or the like is utilized in the pump 21. While the capsules 41 are magnetic, they are made to flow by bloodstream when their magnetic susceptibility is low; in this case, therefore, they would not be trapped by the magnetic force of the pump 21 to remain in the pump 21.

In the case where the capsules 41 are so high in magnetic susceptibility that they might remain trapped in the pump 21, they can be prevented from entering into the ventricular assist system 20, by constantly generating DC magnetic fields by the electromagnets 25 arranged for guiding the capsules 41. Or, alternatively, a permanent magnet 29 may be disposed at the conduit 22*a* connected to the inlet (inflow port) of the pump 21, whereby the capsules 41 can be trapped on the upstream side of the inlet of the ventricular assist system 20. In this case, therefore, the capsules 41 can be prevented from entering the pump 21 to cause a trouble.

While the ventricular assist system has been described in the context of a cardiac assist system in the embodiment described above, the disclosure here is applicable not only to the ventricular assist system but also to, for example, an embedded type defibrillator. Specifically, by connecting electromagnets 25 and an embedded type defibrillator to each other by cables 23, it is possible to guide magnetic capsules and break the capsules. In this case, the electrode to be adhered to the surface of a heart corresponds to the cardiac activity assisting unit.

The principles, embodiments and modes of operation of the apparatus have been described in the foregoing specification, but the invention which is intended to be protected is not to be construed as limited to the particular embodiments of the apparatus disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method of assisting heart activity comprising;
    fluidly connecting a cardiac activity assisting unit to a heart in a living body;
    fixing at least one electromagnet to the heart in the living body;
    operating the cardiac activity assisting unit;
    introducing a magnetic capsule into the body, the magnetic capsule containing contents;

producing a magnetic field through use of the at least one electromagnet to move the magnetic capsule towards the at least one electromagnet; and applying a current to break open the magnetic capsule to release the contents.

2. The method according to claim 1, wherein the heart comprises an aorta and a left ventricle, the connecting of the cardiac activity assisting unit to the heart comprises embedding the cardiac activity assisting unit in the body and connecting the cardiac activity assisting unit to the aorta and the left ventricle.

3. The method according to claim 1, wherein the at least one electromagnet is attached to a sheet, and the fixing of the at least one electromagnet to the heart comprises securing the sheet to the heart.

4. The method according to claim 1, wherein the connecting of the cardiac activity assisting unit to the heart comprises connecting a pump to the heart.

5. The method according to claim 1, wherein the fixing of the at least one electromagnet to the heart comprises fixing a plurality of electromagnets to the heart.

6. The method according to claim 1, wherein the contents in the magnetic capsule comprises cells effective for regeneration of cardiac muscles, the breaking open of the magnetic capsule releasing the cells effective for regeneration of cardiac muscles to an infarct region.

7. The method according to claim 1, wherein the producing of the magnetic field through use of the at least one electromagnet comprises supplying DC current to the at least one electromagnet.

8. The method according to claim 7, wherein the breaking open of the magnetic capsule to release the contents comprises supplying AC current to the at least one electromagnet.

9. A cardiac assist system for assisting activity of a heart, the cardiac assist system comprising:

an electromagnet configured to be fixed to a surface of the heart;

a cardiac activity assisting unit configured to be connected to the heart and to transmit a first electrical current and a second electrical current different from the first electrical current to the electromagnet, the cardiac activity assisting unit operative to assist the activity of the heart;

a controller electrically connected to the cardiac activity assisting unit and the electromagnet, and operative to control the cardiac activity assisting unit and the electromagnet; and the electromagnet is operative to guide a magnetic capsule to an infarct portion in the body via the first electrical current and to break the capsule via the second electrical current.

10. The cardiac assist system as set forth in claim 9, wherein the cardiac activity assisting unit is a pump configured to be embedded in a body.

11. The cardiac assist system as set forth in claim 9, wherein the controller controls supply of a DC voltage or an AC voltage to the electromagnet.

12. The cardiac assist system as set forth in claim 9, wherein the controller is configured to be disposed exterior of the body.

13. The cardiac assist system as set forth in claim 9, wherein the magnetic capsule is adapted to contain marrow cells or myoblast.

14. The cardiac assist system as set forth in claim 9, wherein a permanent magnet for trapping the capsule at an inlet of the pump is disposed at the inlet.

15. A method of assisting heart activity comprising;

fluidly connecting a cardiac activity assisting unit to a heart in a living body;

fixing at least one electromagnet to the heart in the living body;

operating the cardiac activity assisting unit;

introducing a magnetic capsule into the body, the magnetic capsule containing contents;

producing a magnetic field through use of the at least one electromagnet by applying a first electrical current to move the magnetic capsule towards the at least one electromagnet; and breaking open the magnetic capsule to release the contents by applying a second electrical current different from the first electrical current to the at least one electromagnet.

16. A method of assisting heart activity comprising;

fluidly connecting a cardiac activity assisting unit to a heart in a living body;

fixing at least one electromagnet to the heart in the living body;

operating the cardiac activity assisting unit;

introducing a magnetic capsule into the body, the magnetic capsule containing contents;

producing a magnetic field through use of the at least one electromagnet to move the magnetic capsule towards the at least one electromagnet; and breaking open the magnetic capsule to release the contents; wherein the producing of the magnetic field through use of the at least one electromagnet comprises supplying DC current to the at least one electromagnet; and breaking open of the magnetic capsule to release the contents comprises supplying AC current to the at least one electromagnet.

* * * * *